United States Patent [19]

Gatto

[11] Patent Number: 5,102,934

[45] Date of Patent: Apr. 7, 1992

[54] TERTIARY SULFONAMIDE ANTIOXIDANTS

[75] Inventor: Vincent J. Gatto, Baton Rouge, La.

[73] Assignee: Ethyl Corporation, Richmond, Va.

[21] Appl. No.: 670,333

[22] Filed: Mar. 15, 1991

Related U.S. Application Data

[63] Continuation-in-part of Ser. No. 518,846, May 3, 1990, abandoned.

[51] Int. Cl.$^5$ .................................................. C08K 5/43
[52] U.S. Cl. ...................................... 524/169; 106/186; 252/47.5; 252/402; 530/427; 564/92; 564/99
[58] Field of Search ............... 564/92, 99; 252/402, 252/47.5; 524/168, 169; 106/186; 530/427

[56] References Cited

U.S. PATENT DOCUMENTS

| | | | |
|---|---|---|---|
| 2,236,168 | 3/1941 | Dietrich | 252/47.5 |
| 3,329,714 | 7/1967 | Martin | 106/186 |
| 3,506,711 | 4/1970 | Tesoro et al. | 106/186 |
| 3,703,487 | 11/1972 | Green et al. | 106/186 |
| 3,780,103 | 12/1973 | Knell | 252/402 |
| 3,927,091 | 12/1975 | Huber-Emden et al. | 252/402 |
| 3,966,194 | 12/1976 | Gencarelli et al. | 564/99 |
| 4,013,621 | 3/1977 | Knell | 564/92 |
| 4,132,702 | 1/1979 | Schmidt et al. | 524/84 |

FOREIGN PATENT DOCUMENTS

| | | | |
|---|---|---|---|
| 033178 | 9/1974 | Japan | 564/92 |
| 7905000 | 3/1980 | Netherlands . | |

Primary Examiner—Glennon H. Hollrah
Assistant Examiner—Scott C. Rand
Attorney, Agent, or Firm—Patricia J. Hogan

[57] ABSTRACT

Organic materials which are normallly susceptible to oxidative deterioration are stabilized with tertiary sulfonamide antioxidants corresponding to the formula:

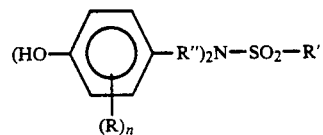

wherein R and R' are independently selected from alkyl, aryl, and benzyl groups, R" is an alkylene group containing 1-5 carbons, and n is an integer of 1-3.

12 Claims, No Drawings

TERTIARY SULFONAMIDE ANTIOXIDANTS

CROSS REFERENCE TO RELATED APPLICATIONS

This application is a continuation-in-part of application Ser. No. 518,486, filed May 3, 1990, now abandoned.

FIELD OF THE INVENTION

The invention relates to tertiary sulfonamides which are useful as antioxidants.

BACKGROUND

As disclosed in U.S. Pat. Nos. 3,780,103 (Knell), 3,927,091 (Huber-Emden et al.), 3,996,194 (Gencarelli et al.), and 4,132,702 (Schmidt et al.) and Netherlands Patent Application 7905000 (Cincinnati Milacron Chemicals), it is known that some amides containing substituted hydroxyphenyl groups have been found to be useful as stabilizers for organic materials which are normally susceptible to oxidative deterioration.

SUMMARY OF INVENTION

The present invention resides in the use as antioxidants of novel tertiary sulfonamides corresponding to the formula:

(p—HO—C$_6$R$_n$H$_{4-n}$—R")$_2$N—SO$_2$—R' wherein R and R' are independently selected from alkyl, aryl, and benzyl groups, R" is an alkylene group containing 1-5 carbons, and n is an integer of 1-3.

The compositions of the invention are compositions comprising organic materials which are normally susceptible to oxidative deterioration and antioxidant amounts of the novel tertiary sulfonamides.

DETAILED DESCRIPTION

The novel tertiary sulfonamides of the compositions of the invention are N,N-disubstituted sulfonamides in which the alkyl substituent para to the hydroxy group in each of the N-substituents may have a branched or unbranched chain but is preferably such that the R" of the formula is a —(CH$_2$)$_m$— group in which m is an integer of 1-5, most preferably 2-5.

As indicated by the formula, the novel tertiary sulfonamides used in the practice of the invention may be derivatives of aliphatic or aromatic sulfonamides, although it is generally preferred that they be derivatives of aliphatic sulfonamides, i.e., compounds in which R' of the formula is an alkyl group, most preferably an alkyl group of 1-20 carbons. Also, although the R substituents on the p-hydroxyphenylalkyl groups may be 1-3 in number; may be alkyl, aryl, or benzyl; and, when there is more than one, may be the same or different, it is usually preferred that there be two substituents, which are most commonly alkyl groups containing 1-6 carbons (preferably 1-4 carbons), in the positions ortho to the hydroxy group.

Exemplary of the novel tertiary sulfonamides are the methanesulfonamides, propanesulfonamides, and benzenesulfonamides in which the N-substituents are β-(3,5-di-t-butyl-4-hydroxyphenyl-ethyl β-(3-methyl-5-t-butyl-4-hydroxyphenyl)ethyl, β-(3,5-diphenyl-4-hydroxyphenyl)ethyl, β-(3-benzyl-5-methyl-4-hydroxyphenyl)ethyl, β-(3-t-butyl-4-hydroxyphenyl)ethyl, β-(2-methyl-3,5-di-t-butyl-4hydroxyphenyl)ethyl, β-(3,5-diisopropyl-4-hydroxy-phenyl)ethyl, γ-(3,5-di-t-butyl-4-hydroxyphenyl)propyl, γ-(3-methyl-5-t-butyl-4-hydroxyphenyl)propyl, β-methyl-γ-(3,5-di-t-butyl-4-hydroxyphenyl)propyl, ε-(3-t-butyl-b 4-hydroxyphenyl)pentyl, or the like.

The preferred tertiary sulfonamides used in the invention are N,N-bis[β-(3,5-di-t-butyl-4-hydroxyphenyl)ethyl]methanesulfonamide, N,N-bis[β-(3,5-diisopropyl-4-hydroxyphenyl)ethyl]methanesulfonamide, and N,N-bis[β-(3-methyl-5-t-butyl-4-hydroxyphenyl)ethyl]methanesulfonamide.

The tertiary sulfonamides may be prepared by reacting the appropriate sulfonyl halide corresponding to the formula R'SO$_2$X with the appropriate secondary amine corresponding to the formula:

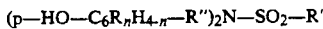

(p—HO—C$_6$R$_n$H$_{4-n}$—R")$_2$NH

X representing halo, preferably chloro or bromo; and R, R', R", and n being as previously defined. Thus, for example, a sulfonyl halide such as methanesulfonyl chloride, 1-butanesulfonyl bromide, 1-pentanesulfonyl chloride, 1-decanesulfonyl chloride, or benzenesulfonyl chloride is reacted with a secondary amine such as bis[β-(3,5-di-t-butyl-4-hydroxyphenyl)ethyl]amine,-bis[γ-(3-methyl-5-t-butyl-4-hydroxyphenyl)propyl]amine, or other such amine.

In the synthesis of the tertiary sulfonamides, the amines and sulfonyl halides are reacted in a mol ratio of about 0.5-1/1, preferably about 0.9/1, in a solvent which is inert to the reaction and which is capable of solubilizing both the reactants and the product and optionally in the presence of an acid scavenger which can neutralize acid produced by the reaction without adversely affecting the process.

Solvents suitable for use in the reaction include, e.g., toluene, benzene, xylene, mesitylene, chlorobenzene, methylene chloride, chloroform, carbon tetrachloride, 1,2-dichloroethane, 1,1,2-trichloroethane, and the like, the preferred solvents usually being toluene and methylene chloride.

Examples of acid scavengers which may be used in the process are triethylamine, tripropylamine, tributylamine, pyridine, and the like, with the preferred acid scavenger being triethylamine. When employed, the acid scavenger is used in an amount such as to provide about one mol of acid scavenger per mol of acid generated by the reaction.

In the preparation of the tertiary sulfonamides, the components of the reaction mixture are combined in any suitable way, conveniently by adding a solution of the amine (and optionally also an acid scavenger) in a portion of the solvent to a solution of the sulfonyl halide in the remainder of the solvent over a period of about 0.5-1 hour while maintaining the reaction mixture at a temperature of about 0°-25° C. Then, when combination of the reactants is at least substantially complete, the temperature is raised, if necessary, to be in the range of about 10°-45° C., preferably about 25°-35° C., and kept in that range for about most convenient in this reaction to use ambient temperature.

After completion of the reaction, the product can be recovered in any suitable way. For example, the reaction mixture may be diluted with solvent, preferably the same solvent as was used in the reaction; the diluted reaction mixture may then be washed with an inorganic acid, such as HCl; the organic phase resulting from this wash may be recovered and washed with a base, such as NaOH; the organic phase resulting from this wash may be recovered and washed with a salt solution, e.g., aqueous NaCl; and the organic phase resulting from this wash ma be recovered and dried to yield the desired tertiary sulfonamide.

In the practice of the invention, the tertiary sulfonamides are used as antioxidants for organic materials which are normally susceptible to oxidative deterioration, such as the organic materials taught in Knell, Huber-Emden et al., Gencarelli et al., and Schmidt et al., the teachings of all of which are incorporated herein by reference.

Although the organic materials that can be stabilized in the practice of the invention include various materials such as hydrocarbon and ester lubricants, plasticizers, epoxy resins, polycarbonates, polyurethanes, polyureas, polyamides, polyesters, polyethers, phenol-formaldehyde resins, urea-formaldehyde resins, melamine-formaldehyde resins, natural polymers (e.g., cellulose, rubber, proteins, and their derivatives), and so forth, those which are most beneficially stabilized are synthetic polymers such as:

(1) polymers and interpolymers of ethylenically-unsaturated hydrocarbons, such as ethylene, propylene, butylene, isobutylene, styrene, butadiene, and piperylene, including the homopolymers, copolymers, and other interpolymers thereof with one another, and copolymers and interpolymers of at least one of them with one or more copolymerizable non-hydrocarbons, such as vinyl acetate, acrylonitrile, methacrylonitrile, methyl acrylate, and methyl methacrylate, (2) halogen-containing polymers, such as polyvinyl chloride and fluoride, polyvinylidene chloride, vinyl chloridevinylidene chloride copolymers, polychloroprene, and chlorinated rubbers, (3) other vinyl and allyl polymers, such as polyvinyl alcohol, acetate, stearate, benzoate, maleate, and butyral, polyallylmelamine, and polyallyl phthalate, and (4) acrylic polymers, such as polyacrylates, polymethacrylates, polyacrylamides, polyacrylonitrile, and polymethacrylonitrile.

In a particularly preferred embodiment of the invention, the tertiary sulfonamides are used to stabilize thermoplastic polymers, such as polyethylenes, polypropylenes, and polycarbonates, during processing, e.g., extrusion or injection molding.

The tertiary sulfonamides are combined with the normally oxidizable materials in antioxidant amounts, usually an amount in the range of about 0.005-5%, preferably about 0.01-2%, based on the weight of the organic material.

When used as antioxidants, the tertiary sulfonamides may be employed as the sole stabilizers for the normally-oxidizable organic materials, or they may be used in conjunction with other stabilizers, such as conventional phenolic antioxidants, thioester synergists, etc. Moreover, their activity as antioxidants does not appear to be inhibited by the presence in the organic materials of additives such as those conventionally employed in such materials, e.g., light stabilizers, ultraviolvet light absorbers, metal deactivators, pigments, dyes, lubricants, nucleating agents, fillers, and the like.

The following examples are given to illustrate the invention and are not intended as a limitation thereof. Unless otherwise specified, quantities mentioned in the examples are quantities by weight.

EXAMPLE I

Charge a suitable reaction vessel with 2.9 g of methanesulfonyl chloride and 10 mL of dry toluene. While stirring the reaction mixture and maintaining the temperature at 0°-8° C., slowly add a solution of 9 g of bis[β-(3,5-di-t-butyl-4-hydroxyphenyl)ethyl]amine, 2.7 g of triethylamine, and 30 mL of dry toluene. Then allow the reaction mixture to reach ambient, i.e., room, temperature, and maintain that temperature for four hours.

After completion of the four-hour period, wash the reaction mixture consecutively with 50 mL of 3N HCl, 50 mL of 1N NaOH, and 50 mL of a saturated aqueous NaCl solution, the organic phase being recovered after each wash and then subjected to the next wash. Recover the final washed organic phase, dry, and concentrate in vacuo to provide a crude product containing 97.6 area % of N,N-bis[ββ-(3,5-di-t-butyl-4-hydroxyphenyl)ethyl]methanesulfonamide.

Recrystallize the crude product from 100 mL of heptane. 15 GC analysis shows the recrystallized product to contain >99% of the tertiary sulfonamide, which has a melting point of 132°-134° C. Spectral analyses (H-NMR, $^{13}$C-NMR, IR, GC-MS) confirm the identity of the solid as N,N-bis[β-(3,5-di-t-butyl-4-hydroxyphenyl)ethyl]methanesulfonamide.

EXAMPLE II

Part A

Prepare a blend of polypropylene and 0.05% of calcium stearate as a lubricant. Retain an aliquot of the blend as a control (Blend A and modify another aliquot by blending 0.1% of the product of Example I as an antioxidant to form Blend B.

Part B

Test the compositions of Part A for melt flow index by extruding them in a Brabender twin screw extruder at 150°-245°-245° C. and 30 rpm under nitrogen and then making five passes through a Brabender single screw extruder at 260°-260°-260°-260° C. and 30 rpm with ambient air. The test results are shown below.

| Blend | MFI @ 230° C./2160 g Load Extrusion Passes | | | |
|---|---|---|---|---|
| | TwS | ss1 | ss3 | ss5 |
| A | 9.6 | 28.5 | 96.5 | — |
| B | 4.3 | 6.1 | 8.4 | 10.9 |

What is claimed is:

1. A composition comprising an organic material which is normally susceptible to oxidative deterioration and an antioxidant amount of a tertiary sulfonamide corresponding to the formula:

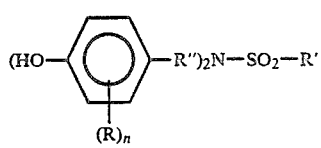

wherein R and R' are independently selected from alkyl, hydrocarbyl, aryl, and benzyl groups, R" is an alkylene group containing 1-5 carbons, and is an integer of 1-3.

2. The composition of claim 1 wherein R is an alkyl group of 1-6 carbons.

3. The composition of claim 2 wherein R is an alkyl group of 1-4 carbons.

4. The composition of claim 3 wherein R is t-butyl.

5. The composition of claim 1 wherein n is 2.

6. The composition of claim 1 wherein R" is $(CH_2)_m$ in which m is an integer of 1-5.

7. The composition of claim 1 wherein R' is an alkyl group of 1-20 carbons.

8. The composition of claim 7 wherein R' is methyl.

9. The composition of claim 1 wherein R is an alkyl group of 1-4 carbons, n is 2, R" is $(CH_2)_m$ in which m is an integer of 1-5, and R' is an alkyl group of 1-20 carbons.

10. The composition of claim 9 wherein the tertiary sulfonamide is N,N-bis[β-(3,5-di-t-butyl-4-hydroxyphenyl)ethyl]methanesulfonamide.

11. The composition of claim 1 wherein the organic material which is normally susceptible to oxidative deterioration is a polymer of an ethylenically-unsaturated hydrocarbon.

12. The composition of claim 11 wherein the tertiary sulfonamide is N,N-bis[β-(3,5-di-t-butyl-4-hydroxyphenyl)ethyl]methanesulfonamide.

* * * * *